US006436027B1

(12) United States Patent
Goldowsky

(10) Patent No.: US 6,436,027 B1
(45) Date of Patent: Aug. 20, 2002

(54) HYDRODYNAMIC BLOOD BEARING

(75) Inventor: Michael Philip Goldowsky, Valhalla, NY (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 09/569,916

(22) Filed: May 11, 2000

(51) Int. Cl.$^7$ ............................................. A61N 1/362
(52) U.S. Cl. ............................................................ 600/16
(58) Field of Search ..................... 600/16, 17; 384/100, 384/111, 107, 113, 114, 115, 292, 322, 378

(56) References Cited

U.S. PATENT DOCUMENTS 5,713,670 A    2/1998   Goldowsky
5,924,975 A    7/1999   Goldowsky
6,244,835 B1 * 6/2001   Antaki et al. ................ 417/356

* cited by examiner

*Primary Examiner*—Jeffrey F. Jastrzab
*Assistant Examiner*—Frances P Oropeza
(74) *Attorney, Agent, or Firm*—Francis L. Conte

(57) ABSTRACT

A hydrodynamic blood bearing includes a piston disposed coaxially in a housing bore. The piston includes a cylindrical outer surface journal spaced from the bore to define a first radial gap for receiving blood as a bearing fluid for hydrodynamically supporting the piston. The piston includes two sets of bearing pads axially spaced apart from each other, with each set including circumferentially spaced apart pads for increasing tilt stiffness of the bearing defined by the journal.

17 Claims, 2 Drawing Sheets

HYDRODYNAMIC BLOOD BEARING

BACKGROUND OF THE INVENTION

The present invention relates generally to blood pumps for a living body, and, more specifically, to bearings therein.

U.S. Pat. No. 5,924,975-Goldowsky discloses a blood pump configured as left ventricular assist device (LVAD) for pumping blood in a living body. The pump includes a reciprocating piston inside a housing bore which is bathed entirely in the blood being pumped. The outer surface of the piston defines a journal cooperating with the bore of the housing to effect a hydrodynamic journal bearing for supporting the piston in the housing as it reciprocates.

The main function of the piston is to pump blood through a living body, yet this must be accomplished without damaging that blood. Accordingly, the various features of the piston for effecting its reciprocation must be designed for minimizing blood damage during operation and continuously flushing blood past the piston for preventing stagnation thereof and minimizing blood damage.

The piston is self supported during operation by developing hydrodynamic pressure in the blood within the small radial gap between the piston journal and housing bore defining the journal bearing. The gap must be sufficiently small, on the order of about 1 or 2 mils, for developing hydrodynamic pressure forces, yet cannot be too small which would increase shear forces in the blood and corresponding damage thereto. Furthermore, the bearing gap must be sufficiently sized to permit suitable flushing or wash-out of the blood therethrough for avoiding blood thrombosis due to insufficient washout flowrate.

Correspondingly, an excessive bearing gap greater than a few mils will destroy the hydrodynamic pressure capability of the journal bearing rendering it ineffective.

A nominal bearing gap is sufficiently small for developing hydrodynamic pressure forces during operation yet nevertheless permits a relatively small amount of piston tilting or cocking during transient or steady-state operation of the piston as it reciprocates during operation. Piston tilting locally reduces the bearing gap at the opposite ends of the piston, and must therefore be minimized.

Resistance to piston tilting may be provided by increasing the axial length of the piston itself, yet this in turn increases the overall length of the blood pump which is undesirable for obtaining a blood pump of compact size for being surgically implanted in a patient.

Accordingly, it is desired to improve the tilt resistance or stiffness of the journal bearing supported piston in the blood pump without increasing its overall length and without increasing blood damage during operation.

BRIEF SUMMARY OF THE INVENTION

A hydrodynamic blood bearing includes a piston disposed coaxially in a housing bore. The piston includes a cylindrical outer surface journal spaced from the bore to define a first radial gap for receiving blood as a bearing fluid for hydrodynamically supporting the piston. The piston includes two sets of bearing pads axially spaced apart from each other, with each set including circumferentially spaced apart pads for increasing tilt stiffness of the bearing defined by the journal.

DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
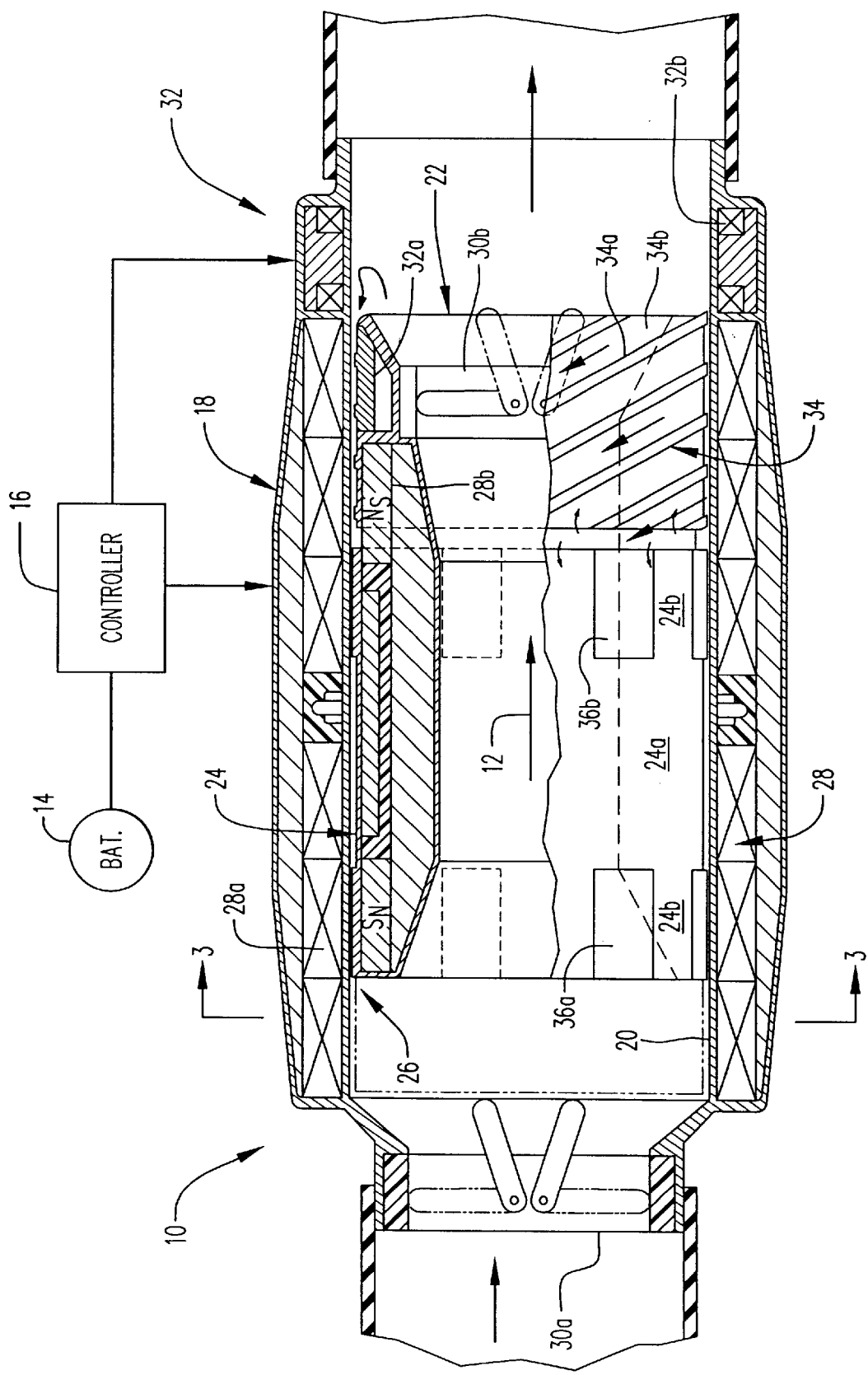
FIG. 1 is an axial, partly sectional view of a linear blood pump having a reciprocating piston supported in a housing bore by a journal bearing in accordance with an exemplary embodiment of the present invention.

Illustrated in FIG. 1 is a linear blood pump 10 configured for being implanted into a living body for pumping blood 12. The basic construction and operation of the pump 10 is disclosed in U.S. Pat. No. 5,924,975, incorporated herein by reference, and is suitably modified in accordance with the present invention for increasing journal bearing tilt stiffness during operation.

The pump is electrically powered by a battery 14 and controlled by an electrical controller 16 suitably electrically joined thereto.

The pump includes a hollow housing 18 which is tubular with a coaxial center bore 20 therein. A tubular piston 22 is disposed coaxially in the housing bore, and includes a smooth cylindrical outer surface or journal 24 spaced radially inwardly from the housing bore to define a hydrodynamic blood bearing 26 for hydrodynamically supporting the piston in the housing during reciprocation thereof.

Means in the form of a linear motor 28 are provided for axially reciprocating the piston inside the housing bore. The linear motor includes a plurality of axially adjoining, coaxial stator drive coils 28a disposed inside the housing, which cooperate with a pair of axially spaced apart permanent magnet rings 28b disposed inside the piston. The magnet rings are spaced radially inwardly of the drive coils for magnetically cooperating therewith to axially translate or oscillate the piston in the housing as the controller 16 sequentially powers the drive coils.

The inlet of the housing includes a first one-way or check valve 30a, and a second one-way check valve 30b is mounted at the downstream end of the piston inside its central bore. As the piston axially reciprocates during operation, the check valves operate sequentially for pumping the blood 12 unidirectionally through the pump.

Since the entire piston is bathed in blood during operation, a portion of that blood is channeled around the piston into the journal bearing 26 defined with the housing bore. In order to generate hydrodynamic pressure in the blood, means in the exemplary form of a rotary motor 32 are provided in the pump for rotating or spinning the piston 22 in the housing bore 20. The rotary motor 32 is preferably a brushless DC motor independent from the linear motor 28 and is also operatively joined to the controller 16.

In the exemplary embodiment illustrated in FIG. 1, the rotary motor includes an annular rotor magnet 32a disposed in the aft end of the piston, and has a plurality of circumferentially adjoining rotor magnetic poles. A cooperating stator band 32b includes a plurality of circumferentially adjoining rotary-drive spin coils fixedly disposed in the aft end of the housing for magnetically cooperating with the rotor magnet 32a for rotating the piston during operation.

Rotation of the piston during operation develops hydrodynamic pressure in the blood filling the journal bearing 26. In the preferred embodiment illustrated in FIG. 1, means in the form of a screw pump 34 coaxially adjoin the journal 24 at the aft end thereof for pumping blood through the journal bearing 26 for accommodating or making up for leakage of blood from the opposite end of the journal during operation.

The screw pump includes a plurality of circumferentially spaced apart screw threads 34a having respective screw grooves 34b therebetween for channeling the blood therethrough. As the piston rotates during operation, the screw threads pump a portion of the blood, which is carried by the grooves, to feed and pressurize the journal bearing for maintaining its hydrodynamic performance.

Figure 2:
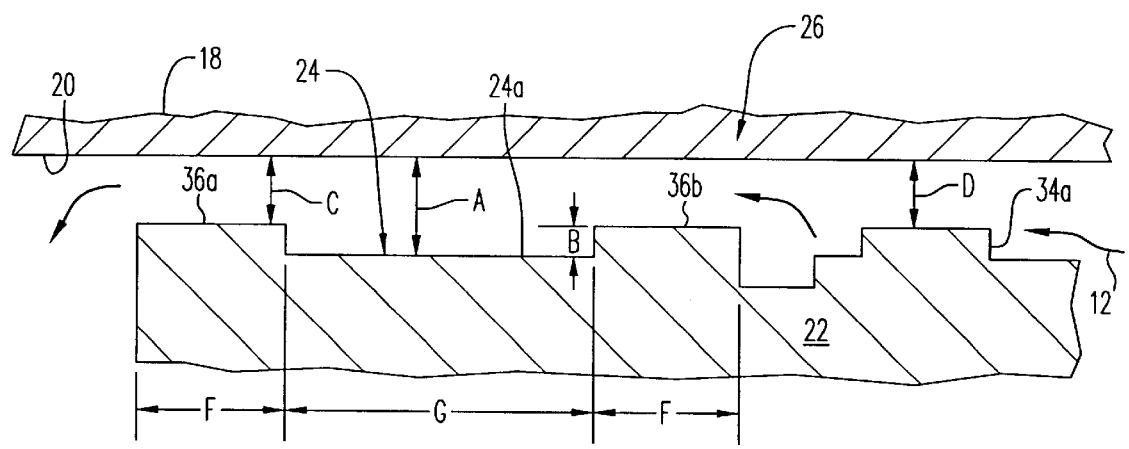
FIG. 2 is an enlarged sectional view of a portion of the journal bearing illustrated in FIG. 1 defined between the piston and bore.

As shown in FIG. 2, the screw pump coaxially adjoins the journal 24 at the aft end of the aft pads 36b for pumping the blood over both the journal and pads to develop the hydrodynamic pressure as the piston rotates.

As indicated above, the basic construction and operation of the blood pump 10 is disclosed in substantial detail in the above identified patent. That pump is improved in accordance with the present invention by specifically improving the journal bearing 26 for introducing therein additional tilt stiffness without compromising the size or performance of the pump for pumping blood without damage thereto.

Figure 3:
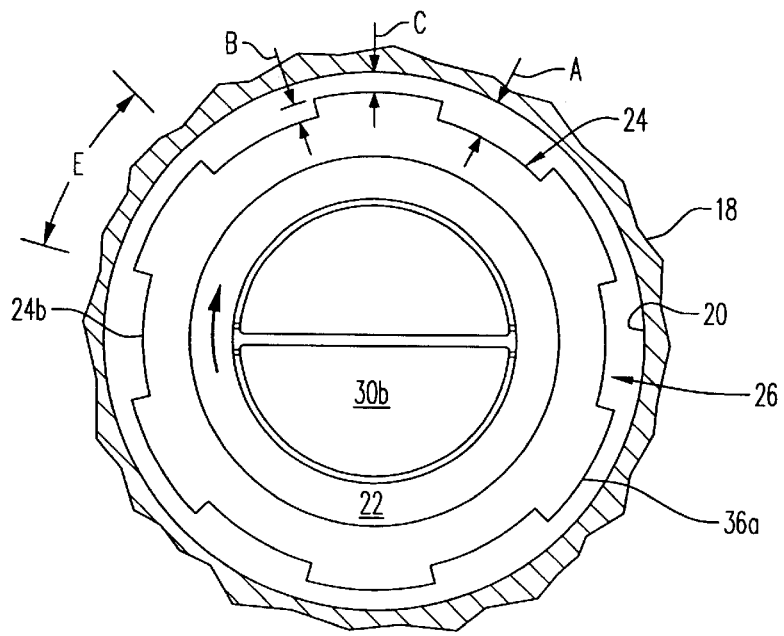
FIG. 3 is a radial sectional end view of the housing and piston illustrated in FIG. 1 and taken along line 3—3 illustrating exemplary tilt-stiffening journal pads therein.

More specifically, a preferred embodiment of the journal bearing 26 in accordance with the present invention is illustrated in more detail in FIGS. 2 and 3. The piston 22 further includes two sets of bearing pads 36a,b axially spaced apart from each other along the journal 24, preferably at opposite ends thereof. Each pad set includes a plurality of the pads circumferentially spaced apart from each other along the journal as illustrated in FIGS. 1 and 3.

As shown in FIG. 2, the journal 24 is spaced radially inwardly with the housing bore 20 to define a first radial or bearing gap A for receiving blood as the bearing fluid, with the magnitude of the first gap A being sufficiently small for generating hydrodynamic pressure for supporting the piston in the housing during operation. The bearing pads 36a,b project radially outwardly from the journal 24 with a radial height B to define a second radial pad gap C with the housing bore, which second gap C is smaller than the first gap A, with the housing bore 20 having a constant internal diameter.

The outer surfaces of the journal 24 and pads 36a,b, and the inner surface defining the housing bore 20 are all smooth and continuous so that as the piston rotates during operation the blood 12 inside the journal bearing 26 develops hydrodynamic pressure over the journal and bearing pads.

The screw pump threads 34a illustrated in FIG. 2 also project radially outwardly and closely adjacent to the housing bore to define a third radial gap D which is preferably equal to the second gap C. The journal bearing 26 itself is provided for hydrodynamically supporting the entire piston including the integral screw pump, and the screw threads 34a may be optimized in height for having a minimal gap D for increasing the efficiency of pumping the blood to supply the journal bearing.

As shown in FIGS. 1 and 2, the two pad sets 36a,b define axially therebetween a center land portion 24a of the journal 24. As shown in FIGS. 1 and 3, the pads in each end set are circumferentially spaced apart from each other to define therebetween end land portions 24b of the journal. The center and end lands 24a,b are preferably coextensive at a common outer diameter of the piston for developing hydrodynamic pressure in the blood for supporting the piston in the bore during operation.

The plain journal 24 without the bearing pads 36a,b develops substantial hydrodynamic pressure during operation and inherent tilt or cocking stiffness for resisting axial cocking moments on the piston during operation, which tilt stiffness would increase as the length of the journal increases.

However, a significant objective for an implantable blood pump is maintaining a compact and small size thereof which necessarily limits the corresponding length of the piston and journal bearing. For a given length of a journal bearing, its tilt stiffness may be otherwise increased by reducing the radial gap A illustrated in FIG. 2. However, this is not desirable for use with the screw pump because this will increase axial flow resistance and decrease washout flowrate, with an increased chance of thrombosis.

By selectively introducing the bearing pads 36a,b over only a portion of the journal 24, and only locally decreasing the radial gap C relative to the journal gap A, a substantial improvement in tilt stiffness may be provided in the journal bearing without compromising blood pump performance or bearing washout. The increased tilt stiffness may be used to advantage in the blood pump having a given length, or the length of the journal, and correspondingly the length of the piston, may be reduced for a given amount of tilt stiffness.

In FIG. 2, the journal gap A cannot be too large or hydrodynamic pressure forces will not be developed, and, the pad gaps C cannot be too small or blood damage may be increased. In an exemplary embodiment, the journal gap A is about 1.5 mils, and the pad height B is up to about ¾ the magnitude of the journal gap A. By limiting the pad height B to less than or equal to about ¾ the journal gap A, significant tilt stiffness may be introduced without damaging the blood or significantly reducing washout of the blood through the journal gap during operation.

As shown in FIGS. 1 and 3, the pads 36a,b are preferably circumferentially equidistantly spaced apart from each other in sets of six pads for example. Each of the pads 36a,b has a circumferential length E, and the pads in each set have a collective circumferential length which is preferably less than about ½ the circumference of the journal 24.

As shown in FIGS. 1 and 2, the pads 36a,b in the two sets are preferably axially aligned with each other at the same circumferential clock positions.

In this way, continuous and substantially straight flowpaths are provided across the entire axial length of the journal 24 for reducing flow obstruction for the blood during operation to ensure effective washout of the blood.

The pads 36a,b preferably have substantially equal axial lengths F, and the journal center land 24a has an axial length G, which is preferably up to about ½ the collective axial lengths 2F+G of the pads and center land.

By introducing the narrow circumferential width pads 36a,b at each end of the journal bearing, a substantially improved bearing geometry is effected for both developing hydrodynamic bearing force during operation as well as enhanced tilt stiffness without compromising bearing performance for use with blood. The central portion of the journal bearing remains unchanged with the same or similar radial gap A as in the original bearing design without the pads 36a,b. The pads at the journal ends effectively reduce the average gap at the ends only of the bearing. The resulting tilt stiffness is essentially that of an entire bearing length of this new average gap since little tilt stiffness is provided by the center section of the journal when it is less than half the overall length.

In an exemplary embodiment, the axial length F of the pads is about 12 mm, with the center land length G being about 26 mm, with the overall length of the journal and pads being about 50 mm. Each of the six pads 36a,b in each set may be about 6 mm in circumferential width E. And the height B of the pads may be selected for reducing the local journal gap at the pads up to about ¾ relative to the journal gap A.

Since tilt stiffness is proportional to the fourth power of axial length, a substantial increase in tilt stiffness is effected by using this exemplary embodiment of the pads which achievesabout 94% of the tilt stiffness of the entire journal having the average of gaps B and C. Since the pads 36a,b are circumferentially spaced apart from each other they maintain substantial flowpaths therebetween which maintains relatively low flow resistance for channeling the blood fluid therethrough for ensuring effective washout blood flow between the pads. The pads in this exemplary embodiment minimally increase total flow resistance to axial blood flow by only about 15%. Tilt stiffness, however, is increased 100% for the same total length of the journal bearing.

This doubling of tilt load capacity may be used for greater design safety factor, or the bearing length may be decreased if a shorter piston is desired.

Although the shear rate for the blood flowing through the pad gaps increases due to the smaller radial gap C, the blood traverses the relatively small pads in a correspondingly short time which offsets the increased shear rate. As shear rate duration decreases for blood, the magnitude of shear that the blood may tolerate without blood cell damage or hemolysis also increases. Within practical limits, the pad geometry and gap may be optimized so as not to increase blood damage.

Testing of the improved journal bearing with pads resulted in the same low level of blood damage as a plain cylindrical bearing without the pads, yet twice the tilt stiffness was obtained. In order to reduce blood damage from the projecting pads, the edges of the pads themselves may be chamfered at about 10° to eliminate the otherwise sharp edges. However, chamfering is not required for bearing pads 36a,b having gaps C from about 0.5 to several mils.

The individual pads, 36a,b may be machined in place as a one-piece or unitary construction with the remainder of the piston. Such a unitary piston may be formed entirely of titanium without any undesirable seams therein for ensuring smooth flow of blood. If desired, a coating of carbon may be deposited over the piston and pads. Alternatively, titanium nitride may be sputtered on titanium to form the pads 36a,b with high dimensional precision.

The simple introduction of the small and short pads 36a,b in the otherwise plain journal bearing substantially increases tilt stiffness of the bearing while maintaining hydrodynamic pressure over the entire journal without significantly increasing blood damage or axial flow resistance. Washout blood flow remains substantially unobstructed by the spaced apart pads. And, transient start up of the bearing is also significantly improved since oscillations are quickly damped relative to a plain journal bearing without the pads.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by letters patent of the united states is the invention as defined and differentiated in the following claims in which I claim:

1. A hydrodynamic blood bearing comprising:
    a housing having a bore;
    a piston disposed coaxially in said bore, and having a cylindrical outer surface journal spaced radially inwardly from said housing bore to define said hydrodynamic bearing therewith having a first radial gap for receiving blood as a bearing fluid for hydrodynamically supporting said piston in said housing; and
    said piston further includes two sets of bearing pads axially spaced apart from each other along said journal, with each set including a plurality of said pads circumferentially spaced apart from each other around said journal, and said pads project radially outwardly from said journal with a height to define a second radial gap with said bore being smaller than said first radial gap.

2. A bearing according to claim 1 wherein said pad sets define axially therebetween a center land of said journal, and said pads define circumferentially therebetween end lands of said journal, and said center and end lands are coextensive for developing hydrodynamic pressure for supporting said piston in said bore.

3. A bearing according to claim 2 wherein said pad height is up-to about ¾ of said first radial gap.

4. A bearing according to claim 2 wherein said pads are equidistantly spaced apart from each other.

5. A bearing according to claim 4 wherein said pads in said two sets are axially aligned with each other.

6. A bearing according to claim 4 wherein said pads have a collective circumferential length in each set less than about ½ the circumference of said journal.

7. A bearing according to claim 2 wherein said pads have substantially equal axial lengths, and said center land has an axial length up to about ½ the collective axial length of said pads and center land.

8. A bearing according to claim 2 further comprising:
    means for rotating said piston in said bore; and
    a screw pump coaxially adjoining said journal at one end of said pads for pumping said blood over said journal and pads for developing said hydrodynamic pressure as said piston rotates.

9. A bearing according to claim 8 further comprising means for axially reciprocating said piston inside said bore.

10. A bearing according to claim 9 wherein said piston is tubular and further includes a valve mounted therein for pumping said blood unidirectionally through said piston as said piston axially reciprocates.

11. A bearing according to claim 10 wherein said pad height is up to about ¾ of said first radial gap.

12. A bearing according to claim 10 wherein said pads are equidistantly spaced apart from each other.

13. A bearing according to claim 12 wherein said pads in said two sets are axially aligned with each other.

14. A bearing according to claim 12 wherein said pads have a collective circumferential length in each set less than about ½ the circumference of said journal.

15. A bearing according to claim 10 wherein said pads have substantially equal axial length, and said center land has an axial length up to about ½ the collective axial length of said pads and center land.

16. A bearing according to claim 10 wherein said pads in said two sets are axially aligned with each other, with said pads in each set being equidistantly spaced apart from each other, and said pad height is up to about ¾ said first radial gap.

17. A bearing according to claim 16 wherein:
    said pads have a collective circumferential length in each set less than about ½ the circumference of said journal; and
    said pads have substantially equal axial lengths, and said center land has an axial length up to about ½ the collective axial length of said pads and center land.

* * * * *